(12) United States Patent
Harlev et al.

(10) Patent No.: US 12,161,399 B2
(45) Date of Patent: *Dec. 10, 2024

(54) DEVICES, SYSTEMS, AND METHODS FOR BALANCING ABLATION ENERGY

(71) Applicant: Affera, Inc., Newton, MA (US)

(72) Inventors: Doron Harlev, Watertown, MA (US); Ilya Bystryak, Watertown, MA (US); Alexander Shrabstein, Watertown, MA (US); Yanko K. Sheiretov, Watertown, MA (US); Joseph Harlev, Watertown, MA (US); Paul B. Hultz, Watertown, MA (US)

(73) Assignee: AFFERA, INC., Newton, MA (US)

( * ) Notice: Subject to any disclaimer, the term of this patent is extended or adjusted under 35 U.S.C. 154(b) by 164 days.

This patent is subject to a terminal disclaimer.

(21) Appl. No.: 17/935,901

(22) Filed: Sep. 27, 2022

(65) Prior Publication Data

US 2023/0157748 A1 May 25, 2023

Related U.S. Application Data

(63) Continuation of application No. 16/493,288, filed as application No. PCT/US2018/021545 on Mar. 8, 2018, now Pat. No. 11,490,958.

(Continued)

(51) Int. Cl.
*A61B 18/14* (2006.01)
*A61B 18/16* (2006.01)
*A61B 18/00* (2006.01)

(52) U.S. Cl.
CPC ............ *A61B 18/1492* (2013.01); *A61B 2018/00357* (2013.01); *A61B 2018/00577* (2013.01);

(Continued)

(58) Field of Classification Search
CPC ............ A61B 18/1492; A61B 18/16; A61B 2018/00357; A61B 2018/00577;
(Continued)

(56) References Cited

U.S. PATENT DOCUMENTS 3,683,923 A 8/1972 Anderson
4,657,015 A 4/1987 Irnich
(Continued)

FOREIGN PATENT DOCUMENTS

DE 19717411 A1 11/1998
WO 2018165425 A1 9/2018
WO 2019108479 A1 6/2019

OTHER PUBLICATIONS

ISA, "PCT Application No. PCT/US2018/021545, International Search Report and Written Opinion mailed Jun. 18, 2018", 18 pages.
(Continued)

*Primary Examiner* — Khadijeh A Vahdat
(74) *Attorney, Agent, or Firm* — Tarolli, Sundheim, Covell & Tummino LLP

(57) ABSTRACT

Devices, systems, and methods of the present disclosure are directed to controlling distribution of electrical energy moving from an ablation electrode at a treatment site within a patient to a plurality of return electrodes on skin of the patient. Control over the distribution of electrical energy moving from the ablation electrode to the plurality of return electrodes can reduce or eliminate the need for manual intervention (e.g., repositioning the plurality of return electrodes on the skin of the patient, repositioning the patient, etc.) to achieve a suitable distribution of the electrical energy. Additionally, or alternatively, the devices, systems, and methods of the present disclosure can respond rapidly and automatically to changes in distribution of the electrical energy to reduce the likelihood and magnitude of inadver- (Continued)

tent changes in the distribution of electrical energy over the course of a medical procedure.

23 Claims, 7 Drawing Sheets

Related U.S. Application Data

(60) Provisional application No. 62/468,879, filed on Mar. 8, 2017.

(52) U.S. Cl.
CPC .............. *A61B 2018/00767* (2013.01); *A61B 2018/00875* (2013.01); *A61B 2018/165* (2013.01); *A61B 2018/167* (2013.01)

(58) Field of Classification Search
CPC ........... A61B 2018/00767; A61B 2018/00875; A61B 2018/165; A61B 2018/167
See application file for complete search history.

(56) References Cited

U.S. PATENT DOCUMENTS

| | | | |
|---|---|---|---|
| 5,277,201 A | 1/1994 | Stern | |
| 5,423,808 A | 6/1995 | Edwards et al. | |
| 5,573,533 A | 11/1996 | Strul | |
| 5,827,276 A | 10/1998 | LeVeen et al. | |
| 6,139,546 A | 10/2000 | Koenig et al. | |
| 6,190,381 B1 | 2/2001 | Olsen et al. | |
| 6,258,085 B1 | 7/2001 | Eggleston | |
| 6,319,249 B1 | 11/2001 | Töllner | |
| 6,740,080 B2 | 5/2004 | Jain et al. | |
| 7,736,359 B2 | 6/2010 | McPherson | |
| 7,879,029 B2 | 2/2011 | Jimenez | |
| 8,364,237 B2 | 1/2013 | Stone et al. | |
| 8,449,536 B2 | 5/2013 | Selig | |
| 11,147,618 B2 | 10/2021 | Gearheart et al. | |
| 11,490,958 B2 | 11/2022 | Harlev et al. | |
| 2004/0206365 A1 | 10/2004 | Knowlton | |
| 2005/0101947 A1 | 5/2005 | Jarrard et al. | |
| 2007/0049919 A1 | 3/2007 | Lee, Jr. et al. | |
| 2007/0167942 A1 | 7/2007 | Rick | |
| 2008/0051777 A1 | 2/2008 | Haemmerich | |
| 2008/0071263 A1 | 3/2008 | Blaha | |
| 2009/0036884 A1 | 2/2009 | Gregg et al. | |
| 2009/0187183 A1 | 7/2009 | Epstein | |
| 2013/0138097 A1 | 5/2013 | Mathur et al. | |
| 2013/0165919 A1 | 6/2013 | Epstein | |
| 2015/0182278 A1 | 7/2015 | Ehninger et al. | |
| 2015/0320478 A1 | 11/2015 | Cosman, Jr. et al. | |
| 2020/0360079 A1 | 11/2020 | Harlev et al. | |

OTHER PUBLICATIONS

ISA, "PCT Application No. PCT/US18/62460, International Search Report and Written Opinion mailed Mar. 14, 2019", 17 pages.
Division of Technical Resources—Office of Research Facilities, "Closed Transition Automatic Transfer Switch", Sep. 2016, National Institutes of Health, Issue 56 (Year: 2016).

DEVICES, SYSTEMS, AND METHODS FOR BALANCING ABLATION ENERGY

CROSS-REFERENCE TO RELATED APPLICATIONS

This application is a continuation of U.S. patent application Ser. No. 16/493,288 (now U.S. Pat. No. 11,490,958), filed on Sep. 11, 2019, which is a National Entry from PCT Application No. PCT/US US2018/021545 filed on Mar. 8, 2018, which claims the benefit of U.S. Provisional Application No. 62/468,879 filed on Mar. 8, 2017, each of which is hereby incorporated by reference in its entirety.

TECHNICAL FIELD

The present technology is generally related to devices, systems, and methods for controlling distribution of electrical energy moving from an ablation electrode at a treatment site within a patient to a plurality of return electrodes on skin of the patient.

BACKGROUND

Catheters are used to deliver electrical energy to tissue as part a variety of procedures related to treatment of medical conditions in patients. In certain applications, return electrodes are placed on skin of the patient to serve as return paths for the electrical energy delivered to the tissue. Multiple return electrodes are often used to dissipate the electrical energy to limit the impact of the electrical energy on tissue away from the site of treatment. To achieve a suitable distribution of the electrical energy returning through the return electrodes, however, it is often necessary to adjust manually the positions of the return electrodes.

BRIEF DESCRIPTION OF THE DRAWINGS

Like reference symbols in the various drawings indicate like elements.

DETAILED DESCRIPTION

Overview

Figure 1:
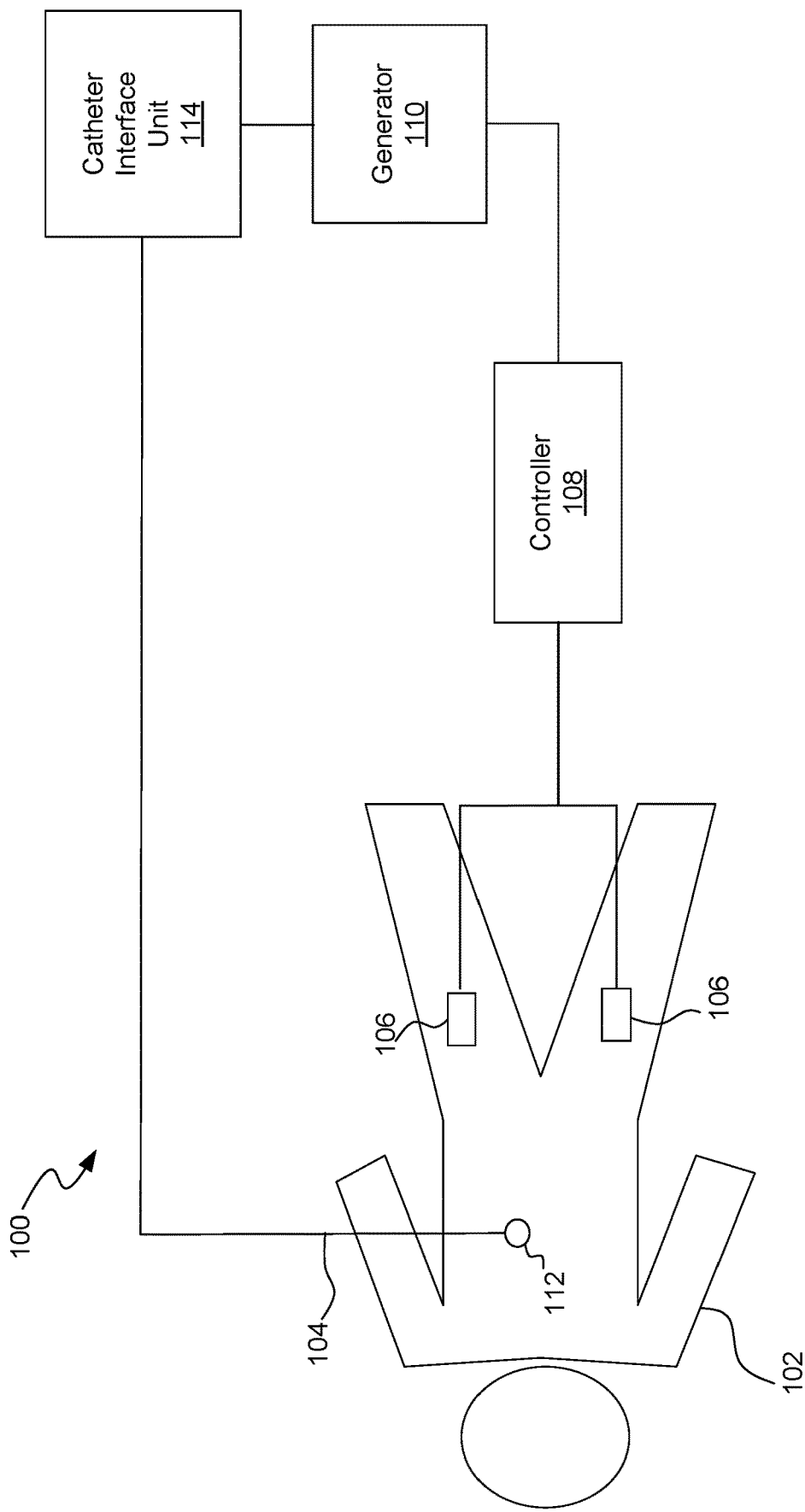
FIG. 1 is a schematic representation of a tissue ablation system configured in accordance with embodiments of the present technology.

The present disclosure is generally directed to devices, systems, and methods of delivering ablation energy to an anatomic structure of a patient in any one or more of various different medical procedures in which ablation energy is delivered to tissue at a treatment site within a patient and returns to a plurality of return electrodes on skin of the patient. For the sake of clarity of explanation, the devices, systems, and methods of the present disclosure are described in the context of cardiac ablation procedures. However, unless otherwise specified or made clear from the context, the devices, systems, and methods of the present disclosure should be understood to be generally additionally, or alternatively, applicable to medical procedures in which an ablation electrode is positioned within a patient and a plurality of return electrodes are positioned on skin of the patient. By way of example, and not limitation, such medical procedures can include ablating tumors in cancer treatment and electro-surgery procedures in which tissue is cut and substantially simultaneously cauterized to avoid or minimize bleeding.

Control over the distribution of electrical energy moving from an ablation electrode to a plurality of return electrodes on skin of the patient can reduce or eliminate the need for manual intervention (e.g., repositioning the plurality of return electrodes on the skin of the patient, repositioning the patient, etc.) to achieve a suitable distribution of the electrical energy. Additionally, or alternatively, the devices, systems, and methods of the present disclosure can respond rapidly and automatically to changes in distribution of the electrical energy to reduce the likelihood and magnitude of inadvertent changes in the distribution of electrical energy over the course of a medical procedure.

In one aspect, a method of ablating tissue includes delivering electrical energy from at least one ablation electrode to tissue at a treatment site within an anatomic structure of a patient, receiving the electrical energy from the at least one ablation electrode at a plurality of return electrodes, the return electrodes external to the patient and in contact with the skin of the patient, and with the plurality of return electrodes in a fixed position in contact with the skin of the patient, controlling a distribution of the electrical energy among the plurality of return electrodes.

In certain implementations, controlling the distribution of the electrical energy can includes controlling a distribution of current among the plurality of return electrodes. Additionally, or alternatively, controlling the distribution of the electrical energy can include controlling a distribution of voltage among the plurality of return electrodes. Further in addition, or further instead, controlling the distribution of the electrical energy can include controlling power distribution among the plurality of return electrodes.

In some implementations, delivering the electrical energy from the at least one ablation electrode to tissue at the treatment site can include ablating tissue in a cardiac chamber of the patient.

In certain implementations, controlling the distribution of the electrical energy among the plurality of return electrodes can include substantially uniformly distributing at least one of current and voltage of the electrical energy among the plurality of return electrodes. Additionally, or alternatively, controlling the distribution of the electrical energy among the plurality of return electrodes includes maintaining an electrode current in each respective return electrode below a predetermined threshold. For example, the predetermined threshold can be less than about 1 ampere.

In some implementations, controlling the distribution of the electrical energy among the plurality of return electrodes can include directing the electrical energy through one or more transformers, each transformer in electrical communication with at least two of the return electrodes. Additionally, or alternatively, controlling the distribution of the electrical energy among the plurality of return electrodes includes switching a path of the electrical energy through one or more resistors in electrical communication with one or more of the return electrodes. Further, or instead, controlling the distribution of the electrical energy among the plurality of return electrodes can include time-division multiplexing the electrical energy between the at least one ablation electrode and the plurality of return electrodes. For example, the electrical energy can be time-division multiplexed between the at least one ablation electrode and each return electrode. By way of further non-limiting example, time-division multiplexing the electrical energy between the at least one ablation electrode and the plurality of return electrodes can include make-before-break switching between the return electrodes.

In certain implementations, controlling the distribution of the electrical energy among the plurality of return electrodes can include generating the electrical energy from a plurality of generators, each generator electrically isolated from each of the other generators, and each generator associated with a respective one of the return electrodes and the at least one ablation electrode. For example, each generator can be electrically isolated from each of the other generators over only a predetermined frequency range.

In another aspect, a tissue ablation system includes a catheter including at least one ablation electrode positionable within an anatomic structure of a patient, a plurality of return electrodes positionable on skin of the patient, at least one generator in electrical communication with the at least one ablation electrode and the plurality of return electrodes to drive electrical energy between the at least one ablation electrode and the plurality of return electrodes, and a controller in electrical communication with the at least one ablation electrode, the plurality of return electrodes, and the at least one generator, wherein the controller is configured to control distribution of the electrical energy among the plurality of return electrodes with the plurality of return electrodes in a fixed position in contact with the skin of the patient.

In some implementations, the controller can be configured to control distribution of current of the electrical energy among the plurality of return electrodes. Additionally, or alternative, the controller can be configured to control distribution of voltage the electrical energy among the plurality of return electrodes. Further, or instead, the controller can be configured to substantially uniformly distribute at least one of the current and the voltage of the electrical energy among the plurality of return electrodes.

In certain implementations, the controller can be configured to maintain at least one of an electrode current and an electrode voltage in each return electrode of the plurality of return electrodes below a predetermined threshold. For example, the predetermined threshold can be less than about 1 ampere.

In some implementations, each of the return electrodes can be releasably securable to skin of the patient.

In certain implementations, the controller can include circuitry through which the electrical energy is distributed to the plurality of return electrodes.

In some implementations, the controller can include a plurality of transformers, each transformer in electrical communication with a respective pair of the return electrodes.

In certain implementations, the controller can include one or more resistors and one or more switches, the one or more switches actuatable to change a path of the electrical energy between the one or more resistors and the plurality of return electrodes.

In some implementations, the controller is configured to time-divide the electrical energy between the at least one ablation electrode and the plurality of return electrodes. For example, the controller can include a multiplexer. Additionally, or alternatively, the multiplexer can include a make-before-break switch.

In certain implementations, the at least one generator includes a plurality of generators electrically isolated from one another, and the controller is configured to control each generator to drive electrical energy between the at least one ablation electrode and a respective return electrode. For example, the generators of the plurality of generators can be electrically isolated from one another over a predetermined frequency range.

The systems and devices of the disclosure are also directed to a tissue ablation system or device comprising:
  a catheter including at least one ablation electrode configured to be positioned within an anatomic structure of a patient;
  a plurality of return electrodes configured to be positioned on skin of the patient;
  at least one generator in electrical communication with the at least one ablation electrode and the plurality of return electrodes configured to drive electrical energy between the at least one ablation electrode and the plurality of return electrodes; and
  a controller in electrical communication with the at least one ablation electrode, the plurality of return electrodes, and the at least one generator, wherein the controller is configured to control distribution of the electrical energy among the plurality of return electrodes with the plurality of return electrodes in a fixed position in contact with the skin of the patient.

The controller can be configured to control distribution of current of the electrical energy among the plurality of return electrodes, to control distribution of voltage the electrical energy among the plurality of return electrodes, to substantially uniformly distribute at least one of the current and the voltage of the electrical energy among the plurality of return electrodes, and/or to maintain at least one of an electrode current and an electrode voltage in each return electrode of the plurality of return electrodes below a predetermined threshold.

The predetermined threshold can be less than about 1 ampere. For example, the predetermined threshold can be less than about 0.9 ampere, 0.8 ampere, 0.7 ampere, 0.6 ampere, 0.5 ampere, 0.4 ampere, 0.3 ampere, 0.2 ampere, 0.1 ampere.

Each of the return electrodes can be configured to be releasably securable to skin of the patient.

The controller can include circuitry through which the electrical energy is distributed to the plurality of return electrodes, a plurality of transformers, each transformer can be in electrical communication with a respective pair of the return electrodes, and/or one or more resistors and one or more switches, the one or more switches can be actuatable to change a path of the electrical energy between the one or more resistors and the plurality of return electrodes.

The controller can be configured to time-divide the electrical energy between the at least one ablation electrode and the plurality of return electrodes.

The controller can include a multiplexer. The multiplexer can include a make-before-break switch.

The at least one generator can include a plurality of generators electrically isolated from one another, and the controller can be configured to control each generator to drive electrical energy between the at least one ablation electrode and a respective return electrode.

The generators of the plurality of generators can be electrically isolated from one another over a predetermined frequency range.

The systems and devices of the disclosure are also directed to their use in a method of ablating tissue, the method comprising:
  delivering electrical energy from the least one ablation electrode to tissue at a treatment site within an anatomic structure of a patient;
  receiving the electrical energy from the at least one ablation electrode at the plurality of return electrodes, the return electrodes external to the patient and in contact with the skin of the patient; and
  with the plurality of return electrodes in a fixed position in contact with the skin of the patient, controlling a distribution of the electrical energy among the plurality of return electrodes.

The methods of the disclosure are also directed to ex vivo methods of controlling a distribution of the electrical energy among a plurality of return electrodes, the method comprising:
  receiving the electrical energy at the plurality of return electrodes from at least one ablation electrode which has pre-delivered electrical energy to tissue at a treatment site within an anatomic structure of a patient, the return electrodes being external to the patient and configured to be in contact with the skin of the patient; and
  with the plurality of return electrodes in a fixed position in contact with the skin of the patient, controlling a distribution of the electrical energy among the plurality of return electrodes.

Controlling the distribution of the electrical energy can include controlling a distribution of current among the plurality of return electrodes, controlling a distribution of voltage among the plurality of return electrodes, controlling power distribution among the plurality of return electrodes, substantially uniformly distributing at least one of current and voltage of the electrical energy among the plurality of return electrodes, and/or maintaining an electrode current in each respective return electrode below a predetermined threshold.

The predetermined threshold can be less than about 1 ampere. For example, the predetermined threshold can be less than about 0.9 ampere, 0.8 ampere, 0.7 ampere, 0.6 ampere, 0.5 ampere, 0.4 ampere, 0.3 ampere, 0.2 ampere, and/or 0.1 ampere.

Controlling the distribution of the electrical energy among the plurality of return electrodes can include directing the electrical energy through one or more transformers, each transformer can be in electrical communication with at least two of the return electrodes.

Controlling the distribution of the electrical energy among the plurality of return electrodes can include switching a path of the electrical energy through one or more resistors in electrical communication with one or more of the return electrodes, and/or time-division multiplexing the electrical energy between the at least one ablation electrode and the plurality of return electrodes.

The electrical energy can be time-division multiplexed between the at least one ablation electrode and each return electrode. Time-division multiplexing the electrical energy between the at least one ablation electrode and the plurality of return electrodes can include make-before-break switching between the return electrodes.

Controlling the distribution of the electrical energy among the plurality of return electrodes can include generating the electrical energy from a plurality of generators, each generator can be electrically isolated from each of the other generators, and each generator can be associated with a respective one of the return electrodes and the at least one ablation electrode.

Each generator can be electrically isolated from each of the other generators over only a predetermined frequency range.

The systems and devices of the disclosure are also directed to their use in an ex vivo method of controlling a distribution of the electrical energy among a plurality of return electrodes, the method comprising:
  receiving the electrical energy at the plurality of return electrodes from at least one ablation electrode which has pre-delivered electrical energy to tissue at a treatment site within an anatomic structure of a patient, the return electrodes being external to the patient and configured to be in contact with the skin of the patient; and
  with the plurality of return electrodes in a fixed position in contact with the skin of the patient, controlling a distribution of the electrical energy among the plurality of return electrodes.

"Ablating tissue" can be understood to mean ablating target tissue to form one or more lesions. Tissue in the proximity of the ablation electrode can be ablated. For example, in the context of cardiac tissue, one or more lesions can interrupt electrical patterns associated with cardia arrhythmia. The methods of the disclosure can reduce or avoid ablation of non-target tissue by controlling the distribution of electrical energy among the plurality of return electrodes.

"Controlling the distribution of the electrical energy" among the plurality of return electrodes as described herein can be through use of a controller. The controller can be in electrical communication with the at least one ablation electrode, the plurality of return electrodes, and/or the at least one generator. The controller can include circuitry through which the electrical energy is distributed to the plurality of return electrodes. The controller can control distribution of the electrical energy among the plurality of return electrodes in a fixed position in contact with skin of the patient. The controller can distribute electrical energy from the ablation electrode to the return electrodes without manual intervention with the return electrodes. The manual intervention that can be avoided can include reducing or eliminating manual repositioning the plurality of return electrodes on the skin of the patient, reducing or eliminating repositioning the patient, etc.

The controller can control the distribution of current, voltage and/or electrical energy among the plurality of return electrodes. The controller can be configured to substantially uniformly distribute at least one of the current and the voltage of the electrical energy among the plurality of return electrodes, and/or to maintain at least one of an electrode current and an electrode voltage in each return electrode of the plurality of return electrodes below a predetermined threshold. The predetermined threshold can be less than about 1 ampere. For example, the predetermined threshold can be less than about 0.9 ampere, 0.8 ampere, 0.7 ampere, 0.6 ampere, 0.5 ampere, 0.4 ampere, 0.3 ampere, 0.2 ampere, and/or 0.1 ampere. Substantially uniform distribution of at least one of current and voltage among the return electrodes can be understood to mean that a respective one of the electrode current and the electrode voltage in the return electrodes is substantially equal.

The controller can include a plurality of transformers. Each transformer can be in electrical communication with a respective pair of the return electrodes.

The controller can include one or more resistors and one or more switches. The one or more switches can be actuatable to change a path of the electrical energy between the one or more resistors and the plurality of return electrodes.

The controller can be configured to time-divide the electrical energy between the at least one ablation electrode and the plurality of return electrodes.

The controller can include a multiplexer. The multiplexer can include a make-before-break switch.

The controller can be configured to control the generator(s) to drive electrical energy between the at least one ablation electrode and a respective return electrode. The at least one generator can include a plurality of generators electrically isolated from one another.

At least one "ablation electrode" can be used to deliver energy to a target tissue and deliver energy to a plurality of return electrodes. The ablation electrode can be delivered to the target site by means of a catheter or other means envisaged by the skilled person. The ablation electrode can be expandable or non-expandable. For example, the ablation electrode can be self-expandable and/or balloon expandable. The ablation electrode(s) can independently have one or a combination of these features.

A plurality of "return electrodes" can be used to receive energy from an ablation electrode. The return electrodes can be configured to be positioned on the skin of the patient. For example, each one of the return electrodes can be secured in a fixed position on the skin of the patient such that the return electrodes remain in place when subjected to incidental forces. The return electrodes can be releasably secured to skin of the patient. For example, the return electrodes can include an adhesive surface. The respective return electrodes can each independently have one or a combination of these features.

"Plurality" is understood to mean two or more, such as two, three, four, five, etc. For example, a "plurality of return electrodes" means that there can be two or more return electrodes.

"At least one" is understood to mean one or more, such as one, two, three, four, five etc. For example, "at least one ablation electrode" means that there can be one or more ablation electrodes, and "at least one generator" means that there can be one or more generators.

Other aspects, features, and advantages will be apparent from the description and drawings, and from the claims. It will also be appreciated that the above implementations can be combined with one another in any reasonable manner in the methods, systems and devices of the disclosure.

Tissue Ablation Systems and Associated Methods

FIG. 1 is a schematic representation of a tissue ablation system 100 during an ablation treatment being performed on a patient 102. The tissue ablation system 100 can include a catheter 104, return electrodes 106, a controller 108, and a generator 110 in electrical communication with one another. The catheter 104 includes an ablation electrode 112 and, in use, the ablation electrode 112 is positioned in contact with tissue in an anatomic structure (e.g., a heart chamber) of the patient 102. Electrical energy from the generator 110 is delivered to the tissue through the ablation electrode 112, the electrical energy moves from the tissue of the anatomic chamber of the patient 102 to the return electrodes 106 positioned on skin of the patient 102, and, ultimately, the electrical energy returns to the generator 110 to complete the circuit formed by the tissue ablation system 100. As described in greater detail below, the controller 108 controls distribution of the electrical energy among the return electrodes 106 in a fixed position in contact with skin of the patient 102. Accordingly, the controller 108 can reduce or eliminate the need to reposition the return electrodes 106 to maintain a desired distribution of electrical energy through the return electrodes 106 during a medical treatment.

In general, the catheter 104 can be intravascularly deliverable to a treatment site (e.g., through insertion in the femoral artery), where the ablation electrode 112 can be positioned relative to tissue at a treatment site. For example, the ablation electrode 112 can be expandable (e.g., self-expandable and/or balloon expandable) or non-expandable for positioning relative to tissue at the treatment site. While such positioning and treatment of tissue through the delivery of electrical energy from the ablation electrode 112 to the tissue can be associated with any one or more of various different medical procedures, the tissue ablation system 100 is herein described in the context of ablating cardiac tissue. For example, the ablation electrode 112 can be positioned in contact with tissue in a heart chamber of the patient 102 such that electrical ablation energy is delivered from the ablation electrode 112 to targeted tissue to form one or more lesions. The one or more lesions can be useful, for example, for interrupting electrical patterns associated with cardiac arrhythmia. Additionally, or alternatively, while the ablation electrode 112 is described as a single electrode, it should be appreciated that the ablation electrode 112 can be a plurality of ablation electrodes.

The generator 110 can drive current from the ablation electrode 112 to the return electrodes 106. The electrical energy driven by the generator 110 can be sufficient for ablating tissue in proximity to the ablation electrode 112 during a medical treatment. For example, the generator 110 can be a radiofrequency (RF) energy (e.g., any one or more RF energy generators well known in the art) such that the ablation energy delivered by the ablation electrode 112 to the tissue can be RF energy (e.g., in the range of 350-500 kHz). Additionally, or alternatively, the generator 110 can generate electrical energy in other frequency ranges (e.g., microwave or a set of electroporation pulses) suitable for medical treatment.

In certain implementations, the tissue ablation system 100 can additionally, or alternatively, include a catheter interface unit 114 in electrical communication (e.g., wired electrical communication) with the generator 110 and the catheter 104 such that it is between the generator 110 and the ablation electrode 112. The catheter interface unit 114 can include, for example, a graphical user interface to display information (e.g., positional information) about the ablation electrode 112 during treatment. Further, or instead, the catheter interface unit 114 can display information about the electrical energy driven between the ablation electrode 112 and the return electrodes 106 by the generator 110. As a specific example, the catheter interface unit 114 can display information related to whether the tissue ablation system 100 is in a therapy mode and, more specifically, information related to a duration of lesion formation.

The return electrodes 106 can be positionable on the skin of the patient. For example, each one of the return electrodes 106 can be secured in a fixed position on the skin of the patient such that the return electrodes 106 remain in place when subjected to incidental forces, as may be experienced, for example, during repositioning of the patient 102 during the treatment. In certain implementations, each of the return electrodes 106 can include an adhesive surface such that the respective one of the return electrodes 106 can be releasably secured to skin of the patient 102 by placing the adhesive surface in contact with skin of the patient 102.

The return electrodes 106 can be releasably securable to skin of the patient 102 in a configuration in which the return electrodes 106 are spaced apart from one another (e.g., with one of the return electrodes 106 on the back of the patient 102 and another one of the return electrodes 106 on a leg of the patient 102). While the return electrodes 106 are described as including two electrodes, it should be understood that additional return electrodes 106 can be used. For example, the number of the return electrodes 106 can be selected to increase the likelihood that the current passing through any one of the return electrodes 106 is likely to remain below a predetermined threshold (e.g., to reduce the likelihood of damage to skin of the patient) during the treatment.

In general, the return electrodes 106 can be substantially similar to one another. However, unless the distribution of the electrical energy through return electrodes 106 is controlled, differences in the distribution of the electrical energy moving from the ablation electrode 112 through the return electrodes 106 can exist during the medical treatment. Such differences can be attributable, for example, to one or more of normal manufacturing differences between the return electrodes 106, differences in contact area between each one of the return electrodes 106 and skin of the patient 102, and differences in position of the return electrodes 106 relative to the ablation electrode 112. While manual adjustments (e.g., repositioning the return electrodes 106) can be made to address these differences to a degree, such manual adjustments can be time-consuming and disruptive from a workflow perspective, given that power is delivered after the patient has been positioned and the catheter 10 has been inserted and delivered to the treatment site. Additionally, or alternatively, such manual adjustments can continue to be required as conditions change during the medical treatment.

The controller 108 can include circuitry to control distribution of the electrical energy among the return electrodes 106 with the return electrodes 106 in a fixed position in contact with skin of the patient. That is, the controller 108 can distribute electrical energy from the ablation electrode 112 to the return electrodes 106 without requiring manipulation of the return electrodes 106. As used herein, it should be understood that the distribution of electrical energy can include distribution of current, voltage and energy, unless otherwise specified or made clear from the context.

In general, the distribution of the electrical energy by the controller 108 can be any one or more distributions suitable for a particular application. For example, the controller 108 can maintain at least one of an electrode current and an electrode voltage in each of the return electrodes 106 below a predetermined threshold (e.g., below about 1 ampere to reduce the likelihood of damage to tissue). Additionally, or alternatively, the distribution of the electrical energy by the controller 108 can be a substantially uniform distribution of at least one of current and voltage among the return electrodes 106 such that a respective one of the electrode current and the electrode voltage in the return electrodes 106 is substantially equal.

Figure 2:
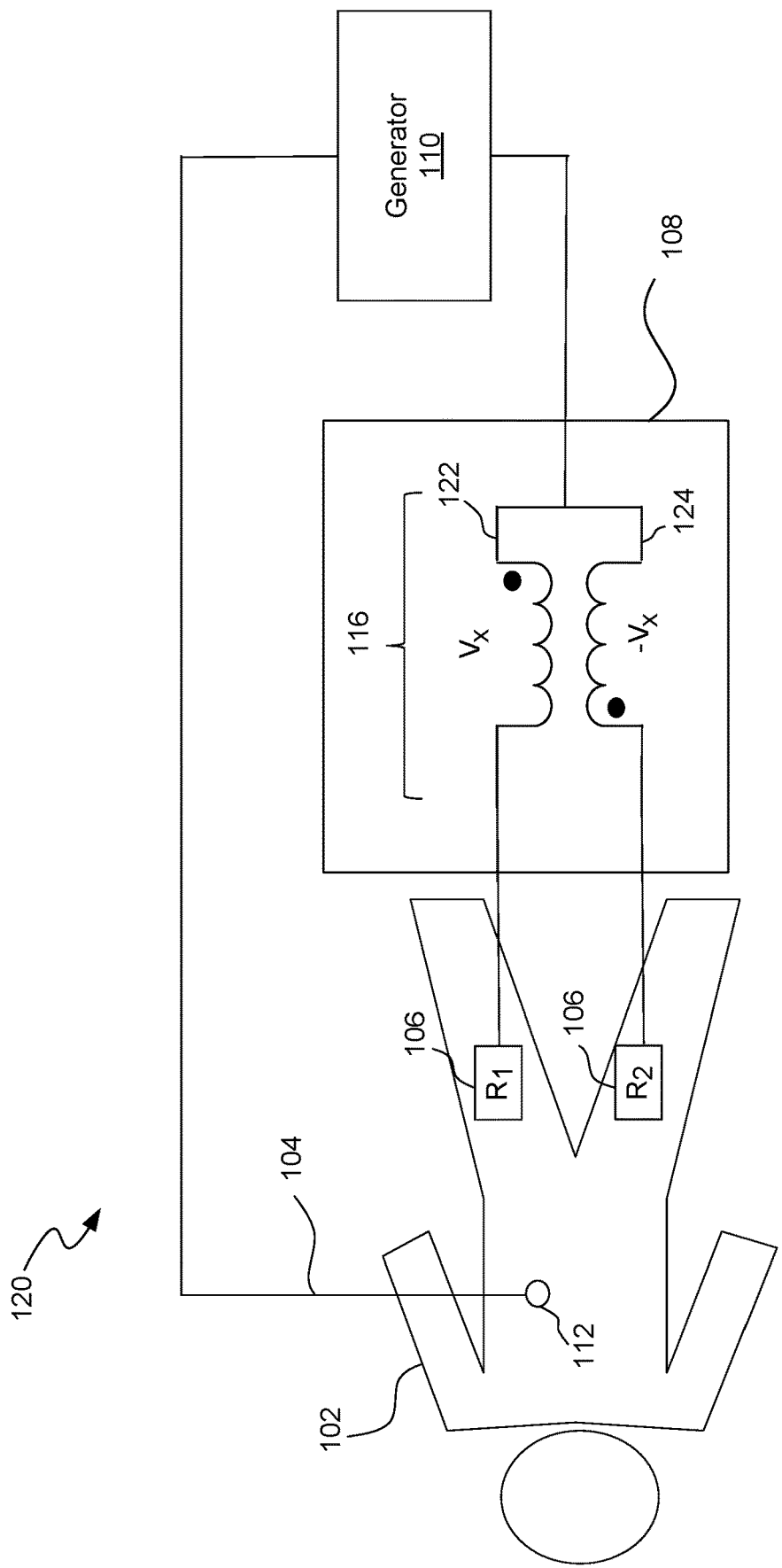
FIG. 2 is an electric circuit diagram of the tissue ablation system of FIG. 1, with the controller including a transformer.

Referring now to FIGS. 1 and 2, the controller 108 can include a transformer 116 in electrical communication with each combination of at least two of the return electrodes 106. It should be understood that because the return electrodes 106 are shown as including a single pair, the transformer 116 is shown as a single transformer in FIG. 2. As described in greater detail below, additional transformers can be used in implementations in which the system includes more than two return electrodes.

Referring now to FIG. 2, an electric circuit 120 represents the flow of electrical energy through the tissue ablation system 100 (FIG. 1) during a medical treatment performed on the patient 102 (FIG. 1). The transformer 116 can include a primary winding 122 and a secondary winding 124. The transformer 116 can be modeled, for example, as an ideal transformer. The primary winding 122 can be in series with a first impedance $R_1$, and the secondary winding 124 can be in series with a second impedance $R_2$. $R_1$ is the impedance associated with one of the return electrodes 106 (FIG. 1) on skin of the patient 102, and $R_2$ is the impedance associated with the other one of the return electrodes 106 (FIG. 1) on skin of the patient 102.

As electrical energy is driven by the generator 110, a voltage V develops across the generator 110. If there is an impedance mismatch between the return electrodes 106, the primary winding 122 will have a voltage $V_x$ and the secondary winding 124 will have a voltage $-V_x$. Accordingly, the voltage across one of the return electrodes 106 will be $V+V_x$ while the voltage across the other one of the return electrodes 106 will be $V-V_x$ such that the current through each of the return electrodes 106 is the same. That is, if there is an impedance mismatch between $R_1$ and $R_2$, the transformer 116 balances the current passing through $R_1$ and $R_2$ such that the current passing through the return electrodes 106 is equal. It should be appreciated that, in the degenerate case in which $R_1$ is equal to $R_2$, $V_x$ is zero.

Figure 3:
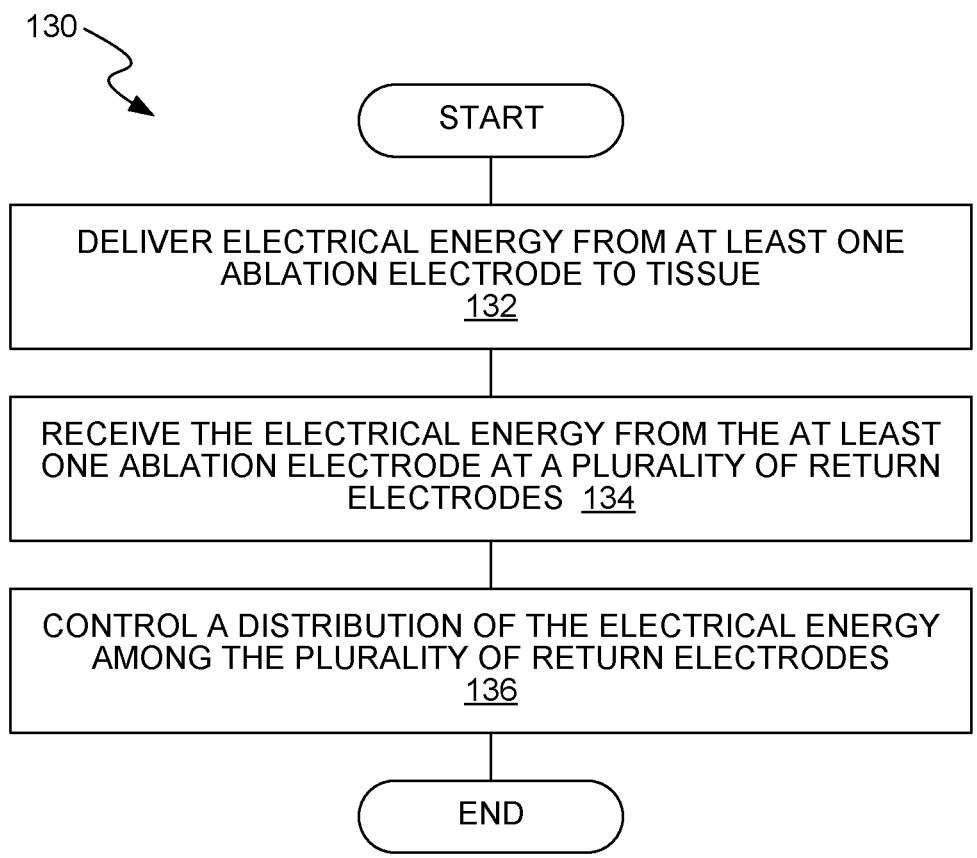
FIG. 3 is a flowchart of a method of ablating tissue in accordance with embodiments of the present technology.

Referring now to FIG. 3, an exemplary method 130 of ablating tissue. Unless otherwise specified or made obvious from the context, the exemplary method 130 can be carried out using any one or more of the systems and devices described herein.

The exemplary method 130 can include delivering 132 electrical energy from at least one ablation electrode to tissue at a treatment site within an anatomic structure of a patient, receiving 134 the electrical energy from the at least one ablation electrode at a plurality of return electrodes, and controlling 136 a distribution of the electrical energy among the plurality of return electrodes. The return electrodes can be external to the patient and in contact with the skin of the patient, and the distribution of the electrical energy can be controlled 136 with the return electrodes in a fixed position in contact with skin of the patient. Thus, for example, the exemplary method 130 can facilitate achieving a desired distribution of the electrical energy without requiring repositioning of the return electrodes.

Delivering 132 electrical energy from the at least one ablation electrode to tissue at the treatment site within the anatomic structure of the patient can include driving the electrical energy from the ablation electrode to the tissue through one or more of the generators described herein (e.g., the generator 110 in FIGS. 1 and 2). For example, delivering 132 the electrical energy from the at least one ablation electrode can include ablating tissue in a cardiac chamber of the patient. Continuing with this example, delivering 132 the electrical energy from the at least one ablation electrode can include forming one or more lesions in the tissue as part of a treatment of cardiac arrhythmias.

Receiving 134 the electrical energy from the at least one ablation electrode at the plurality of return electrodes can include passing the electrical energy from tissue in an anatomic structure of the patient to the return electrodes positioned on skin of the patient. In certain implementations, the electrical energy can be received 134 at the return electrodes at the same time. Further, or instead, as described in greater detail below, the electrical energy can be received 134 at the return electrodes individually (e.g., through time-division multiplexing).

In general, controlling 136 the distribution of the electrical energy among the plurality of return electrodes can include controlling distribution of one or more of current and voltage among the return electrodes. It should be appreciated that controlling 136 the distribution of the electrical energy among the plurality of return electrodes can include directing the electrical energy through any one or more of the controllers described herein. Thus, for example, controlling 136 the distribution of the electrical energy can include directing the electrical energy through one or more transformers (e.g., through the controller 108 shown in FIGS. 1 and 2) in electrical communication with at least two of the return electrodes.

In certain implementations, controlling 136 the distribution of the electrical energy among the plurality of return electrodes can include substantially uniformly distributing at least one of current and voltage of the electrical energy among the plurality of return electrodes. Such a substantially uniform distribution can be useful, for example, for making most efficient use of the return electrodes. That is, the substantially uniform distribution of at least one of current and voltage can facilitate controlling the electrical energy using fewer return electrodes since it reduces the likelihood of excessive current in any one of them.

In some implementations, controlling 136 the distribution of the electrical energy among the plurality of return electrodes can include maintaining an electrode current or an electrode voltage in each respective return electrode below a predetermined threshold. For example, in instances in which an electrode current in each respective return electrode is maintained below a predetermined threshold, the predetermined threshold can be less than about 1 ampere (e.g., about 0.7 amperes). More generally, the predetermined threshold can be associated with reducing the likelihood of a concentration of energy that would cause an unintended change in tissue away from the treatment site.

While certain embodiments have been described, other embodiments are additionally or alternatively possible.

Figure 4:
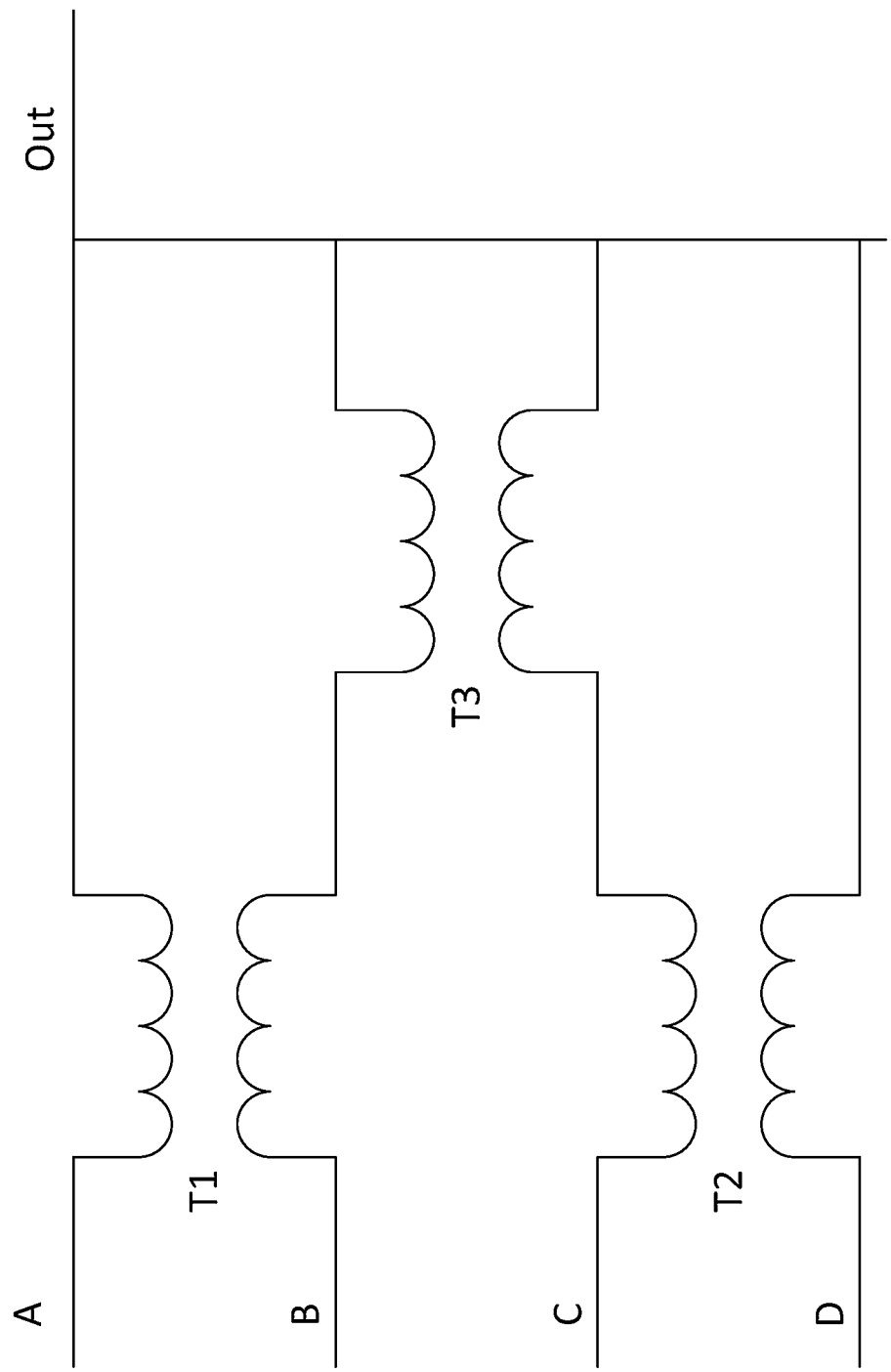
FIG. 4 is a schematic representation of a portion of electrical circuit of an implementation in which energy moving between an ablation electrode and four return electrodes is balanced through an arrangement of three transformers in accordance with an embodiment of the present technology.
Figure 5:
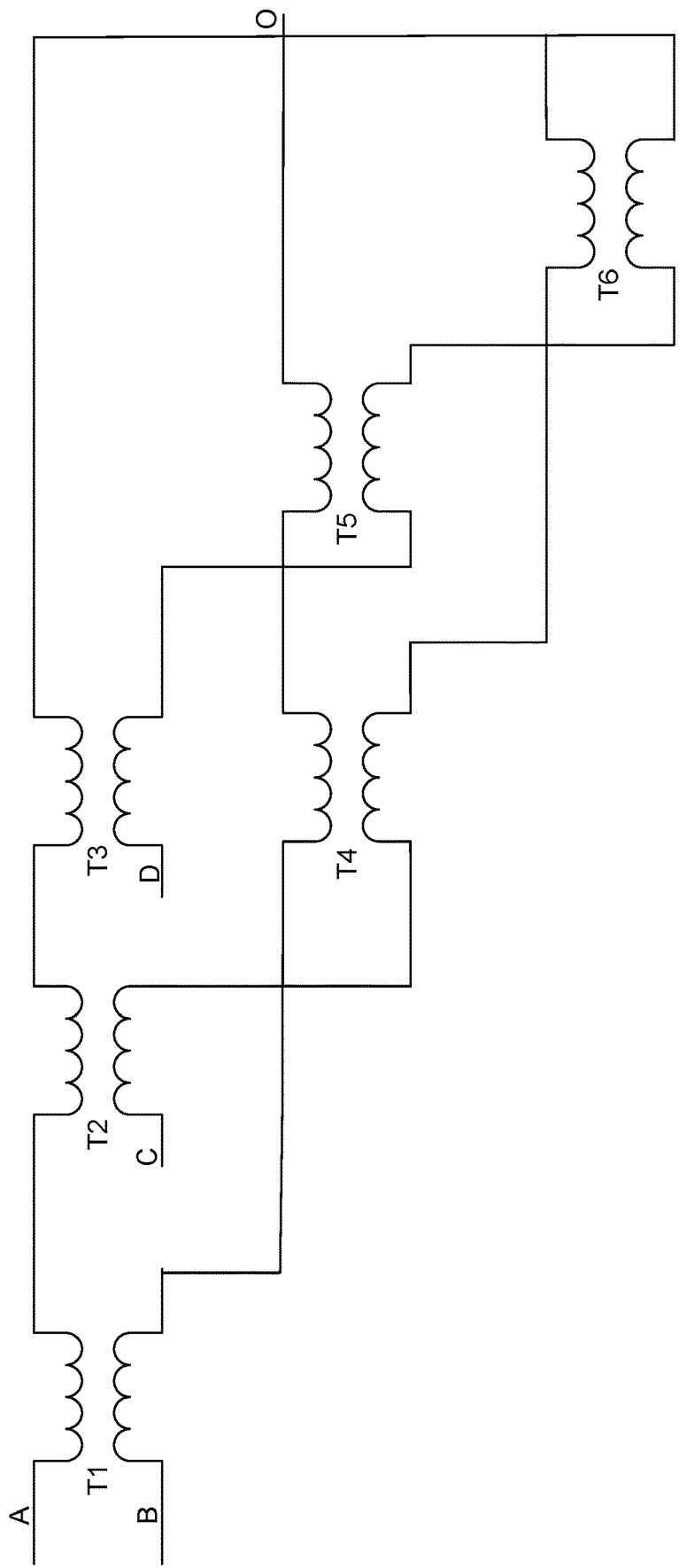
FIG. 5 is a schematic representation of a portion of an electric circuit in which energy from an ablation electrode can be distributed among four return electrodes in accordance with an embodiment of the present technology.

As an example, while the controller has been described as including two return electrodes, it should be appreciated that controllers can additionally, or alternatively, include more than two return electrodes. In general, energy passing through more than two return electrodes can be balanced through the use one or more transformers. Examples of transformer arrangements useful for balancing energy among more than two return electrodes are shown in FIGS. 4 and 5. Unless otherwise indicated or made clear from the context, the return electrodes A, B, C, D should be understood to be identical to the return electrodes 106 (FIGS. 1 and 2), and the transformers T1, T2, T3, T4, T5, and T6 should be understood to be identical to the transformer 116 (FIG. 2).

FIG. 4 is a schematic representation of a portion of an electrical circuit of an implementation in which energy moving between an ablation electrode (e.g., ablation electrode 112 in FIG. 1) and four return electrodes A, B, C, D can be balanced through an arrangement of three transformers T1, T2, T3. In such instances, a first electrode pair A-B can be balanced through the transformer T1, and a second electrode pair C-D can be balanced through the transformer T2. The electrode pairs A-B and C-D can be balanced through the transformer T3 so that all four return electrodes A, B, C, D receive the same current.

Additionally, the controller can include one transformer for each combination of pairs of electrodes in a plurality of return electrodes. FIG. 5 is a schematic of a portion of an electric circuit in which energy from an ablation electrode (e.g., ablation electrode 112 in FIG. 1) can move among four return electrodes A, B, C, D, with each pair of electrodes (A-B, A-C, A-D, B-C, B-D, and C-D) balanced through electrical communication with transformers T1-T6. As compared to the configuration of transformers in FIG. 4, it should be appreciated that the configuration of transformers in FIG. 5 can have a lower residual voltage across each transformer. Additionally, it should be understood that, in FIG. 5, each pair of electrodes is shown separately, rather than depicting multiple connections extending from each return electrode A-D to the transformers T1-T6.

Figure 6:
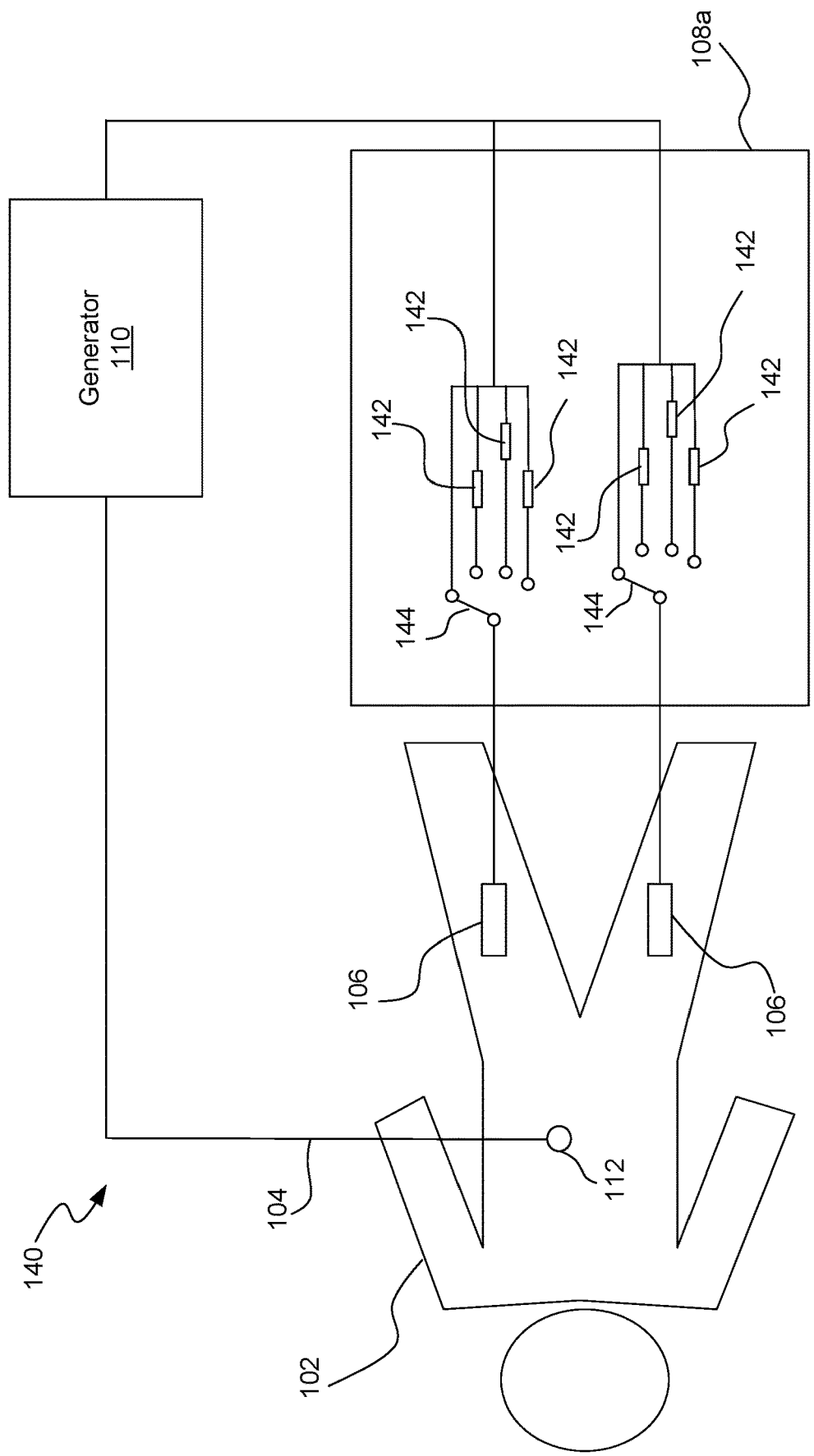
FIG. 6 is an electric circuit diagram of the tissue ablation system of FIG. 1, with the controller including resistors and a switch.

As another example, while a controller has been described as including one or more transformers, it should be appreciated that controllers can additionally, or alternatively, include other electrical components for controlling distribution of electrical energy to a plurality of return electrodes. For example, referring now to FIGS. 1 and 6, an electric circuit 140 represents the flow of electrical energy through the tissue ablation system 100, with a controller 108a including resistors 142 and switches 144 in electrical communication with one another to control one or more of current and voltage through the respective return electrodes 106. Unless otherwise specified or made clear from the context, the controller 108a should be understood to be interchangeable with or used in addition to the controller 108 described with respect to FIG. 2. Further, or instead, unless otherwise specified or made clear from the context, the controller 108a should be understood to be operable as part of the tissue ablation system 100 carrying out any one or more of the methods described herein, including the exemplary method 130 described with respect to FIG. 3.

In use, each switch 144 can be actuatable to change a path of electrical energy in the ablation system 100' to change the resistance associated with a respective one of the return electrodes 106. For example, the resistors 142 can be arranged such that activation of one or more of the switches 144 can connect one or more of the resistors 142 in series with the respective return electrode 106. It should be appreciated that the electrode current in the respective return electrode 106 can decrease as the switch 144 is activated. Additionally, or alternatively, deactivation of one or more of the switches 144 can disconnect one or more of the resistor 142 from connection to the respective return electrode 106. The electrode current in one or more of the return electrodes 106 can increase as the switch 144 is deactivated.

The activation of one or more of the switches 144 can be based on an upper threshold of current detected in one or both of the return electrodes 106. Also, or instead, the deactivation of one or more of the switches 144 can be based on a lower threshold of current detected in one or both of the return electrodes 106. While the one or more of the switches 144 has been described as being normally open, it should be appreciated that the one or more switches 144 can, additionally, or alternatively, be normally closed and/or based on a variety of any one or more inputs.

Figure 7:
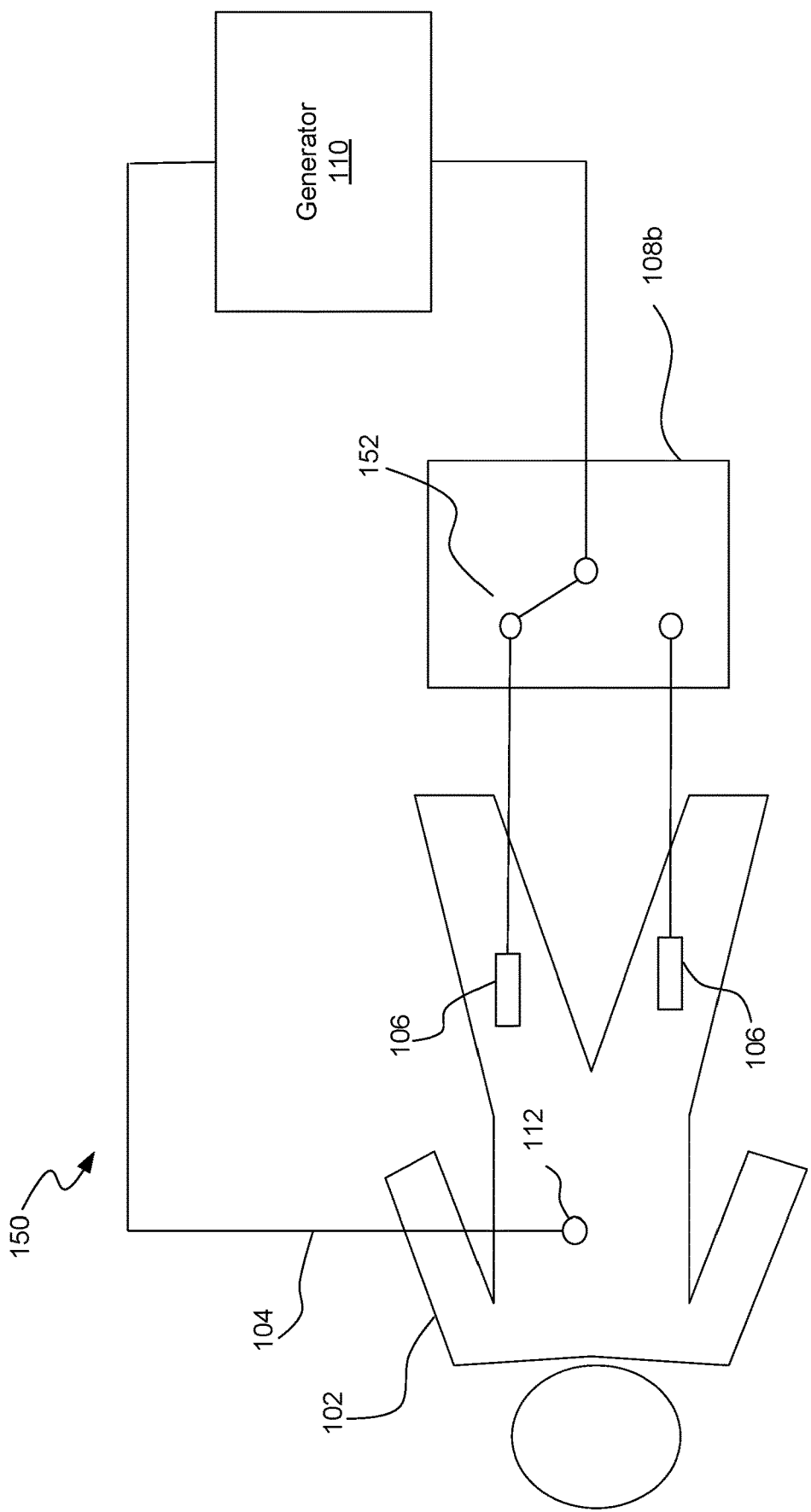
FIG. 7 is an electric circuit diagram of the tissue ablation system of FIG. 1, with a controller including a multiplexer.

As another example, while electrical energy has been described as being applied to return electrodes simultaneously, it should be appreciated that the electrical energy can be time-divided between at least one ablation electrode and a plurality of return electrodes. For example, referring now to FIGS. 1 and 7, an electric circuit 150 represents the flow of electrical energy through the tissue ablation system 100, with a controller 108b including a multiplexer 152 to control one or more of current and voltage through the return electrodes 106. Unless otherwise specified or made clear from the context, the controller 108b should be understood to be interchangeable with or used in addition to one or more of the controller 108 described with respect to FIG. 2 and the controller 108a described with respect to FIG. 6. Further, or instead, unless otherwise specified or made clear from the context, the controller 108b should be understood to be operable as part of the tissue ablation system 100 carrying out any one or more of the various different methods described herein, including the method 130 described with respect to FIG. 3.

Each return electrode 106 can be in electrical communication with the generator 110 through a respective channel of the multiplexer 152. In use, the multiplexer 152 can switch between the channels (e.g., cycling sequentially among the channels) such that each of the return electrodes 106 can be in electrical communication with the generator 110, independently of the electrical communication between the generator 110 and each of the other return electrodes 106. Thus, for example, by rapidly cycling the multiplexer 152 between the return electrodes 106 to make and break electrical communication between the generator 110 and each of the return electrodes 106, one or more of the electrode current and electrode voltage of each of the return electrodes 106 can be controlled independently of the electrical energy delivered to the other return electrodes 106.

In certain implementations, the multiplexer 152 can include a make-before-break switch. During switching between the return electrodes 106, the make-before-break switch can maintain a connection with a first one of the return electrodes 106 until a connection with a second one of the return electrodes 106 is made. As compared to switching before a connection to another one of the return electrodes 106 is made, make-before-break switching can be useful for reducing load fluctuations experienced by the generator 110.

As still another example, while electrical energy has been described as being applied to return electrodes using a single generator, it should be appreciated that the electrical energy can be delivered to each of the return electrodes through a respective generator. For example, referring to FIG. 1, the generator 110 can include a plurality of generators such that each generator is in electrical communication with a respective one of the return electrodes 106 and the ablation electrode 112. In such implementations, the plurality of generators can be electrically isolated from one another. Additionally, or alternatively, the plurality of generators can be electrically isolated from one another over a predetermined frequency range (e.g., a frequency range of the electrical energy directed from the ablation electrode 112 to the tissue during treatment). In certain instances, the controller 108 can control each generator to drive electrical energy between the ablation electrode the respective one of the return electrodes 106.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

Additional Examples

The disclosure will now be defined by reference to the following clauses, which can be combined in any manner in addition to the combinations provided below:

1. A method of ablating tissue, the method comprising:
    delivering electrical energy from at least one ablation electrode to tissue at a treatment site within an anatomic structure of a patient;
    receiving the electrical energy from the at least one ablation electrode at a plurality of return electrodes, the return electrodes external to the patient and in contact with the skin of the patient; and
    with the plurality of return electrodes in a fixed position in contact with the skin of the patient, controlling a distribution of the electrical energy among the plurality of return electrodes.
2. The method of clause 1, wherein controlling the distribution of the electrical energy includes controlling a distribution of current among the plurality of return electrodes.
3. The method of any one of clauses 1 and 2, wherein controlling the distribution of the electrical energy includes controlling a distribution of voltage among the plurality of return electrodes.
4. The method of any one of clauses 1 and 2, wherein controlling the distribution of the electrical energy includes controlling power distribution among the plurality of return electrodes.
5. The method of any one of clauses 1-4, wherein delivering the electrical energy from the at least one ablation electrode to tissue at the treatment site includes ablating tissue in a cardiac chamber of the patient.
6. The method of any one or more of clauses 1-5, wherein controlling the distribution of the electrical energy among the plurality of return electrodes includes substantially uniformly distributing at least one of current and voltage of the electrical energy among the plurality of return electrodes.
7. The method of any one or more of clauses 1-6, wherein controlling the distribution of the electrical energy among the plurality of return electrodes includes maintaining an electrode current in each respective return electrode below a predetermined threshold.
8. The method of clause 7, wherein the predetermined threshold is less than about 1 ampere.
9. The method of any one or more of clauses 1-8, wherein controlling the distribution of the electrical energy among the plurality of return electrodes includes directing the electrical energy through one or more transformers, each transformer in electrical communication with at least two of the return electrodes.
10. The method of any one or more of clauses 1-9, wherein controlling the distribution of the electrical energy among the plurality of return electrodes includes switching a path of the electrical energy through one or more resistors in electrical communication with one or more of the return electrodes.
11. The method of any one or more of clauses 1-10, wherein controlling the distribution of the electrical energy among the plurality of return electrodes includes time-division multiplexing the electrical energy between the at least one ablation electrode and the plurality of return electrodes.
12. The method of clause 11, wherein the electrical energy is time-division multiplexed between the at least one ablation electrode and each return electrode.
13. The method of any one of clauses 11 and 12, wherein time-division multiplexing the electrical energy between the at least one ablation electrode and the plurality of return electrodes includes make-before-break switching between the return electrodes.
14. The method of any one or more of clauses 1-13, wherein controlling the distribution of the electrical energy among the plurality of return electrodes includes generating the electrical energy from a plurality of generators, each generator electrically isolated from each of the other generators, and each generator associated with a respective one of the return electrodes and the at least one ablation electrode.
15. The method of clause 14, wherein each generator is electrically isolated from each of the other generators over only a predetermined frequency range.
16. A tissue ablation system comprising:
    a catheter including at least one ablation electrode positionable within an anatomic structure of a patient;
    a plurality of return electrodes positionable on skin of the patient;
    at least one generator in electrical communication with the at least one ablation electrode and the plurality of return electrodes to drive electrical energy between the at least one ablation electrode and the plurality of return electrodes; and
    a controller in electrical communication with the at least one ablation electrode, the plurality of return electrodes, and the at least one generator, wherein the controller is configured to control distribution of the electrical energy among the plurality of return electrodes with the plurality of return electrodes in a fixed position in contact with the skin of the patient.
17. The system of clause 16, wherein the controller is configured to control distribution of current of the electrical energy among the plurality of return electrodes.
18. The system of any one of clauses 16 and 17, wherein the controller is configured to control distribution of voltage the electrical energy among the plurality of return electrodes.
19. The system of any one of clauses 16-18, wherein the controller is configured to substantially uniformly distribute at least one of the current and the voltage of the electrical energy among the plurality of return electrodes.
20. The system of any one or more of clauses 16-19, wherein the controller is configured to maintain at least one of an electrode current and an electrode voltage in each return electrode of the plurality of return electrodes below a predetermined threshold.
21. The system of clause 20, wherein the predetermined threshold is less than about 1 ampere.
22. The system of any one or more of clauses 16-21, wherein each of the return electrodes is releasably securable to skin of the patient.
23. The system of any one or more of clauses 16-22, wherein the controller includes circuitry through which the electrical energy is distributed to the plurality of return electrodes.
24. The system of any one or more of clauses 16-23, wherein the controller includes a plurality of transformers, each transformer in electrical communication with a respective pair of the return electrodes.
25. The system of any one or more of clauses 16-24, wherein the controller includes one or more resistors and one or more switches, the one or more switches actuatable to change a path of the electrical energy between the one or more resistors and the plurality of return electrodes.

26. The system of any one or more of clauses 16-25, wherein the controller is configured to time-divide the electrical energy between the at least one ablation electrode and the plurality of return electrodes.

27. The system of clause 26, wherein the controller includes a multiplexer.

28. The system of clause 27, wherein the multiplexer includes a make-before-break switch.

29. The system of any one or more of clauses 16-27, wherein the at least one generator includes a plurality of generators electrically isolated from one another, and the controller is configured to control each generator to drive electrical energy between the at least one ablation electrode and a respective return electrode.

30. The system of clause 29, wherein the generators of the plurality of generators are electrically isolated from one another over a predetermined frequency range.

31. A tissue ablation system or device comprising:
 a catheter including at least one ablation electrode configured to be positioned within an anatomic structure of a patient;
 a plurality of return electrodes configured to be positioned on skin of the patient;
 at least one generator in electrical communication with the at least one ablation electrode and the plurality of return electrodes configured to drive electrical energy between the at least one ablation electrode and the plurality of return electrodes; and
 a controller in electrical communication with the at least one ablation electrode, the plurality of return electrodes, and the at least one generator, wherein the controller is configured to control distribution of the electrical energy among the plurality of return electrodes with the plurality of return electrodes in a fixed position in contact with the skin of the patient.

32. The system or device of clause 31, wherein the controller is configured to control distribution of current of the electrical energy among the plurality of return electrodes.

33. The system or device of any one of clauses 31 and 32, wherein the controller is configured to control distribution of voltage the electrical energy among the plurality of return electrodes.

34. The system or device of any one of clauses 31-33, wherein the controller is configured to substantially uniformly distribute at least one of the current and the voltage of the electrical energy among the plurality of return electrodes.

35. The system or device of any one or more of clauses 31-34, wherein the controller is configured to maintain at least one of an electrode current and an electrode voltage in each return electrode of the plurality of return electrodes below a predetermined threshold.

36. The system or device of clause 35, wherein the predetermined threshold is less than about 1 ampere.

37. The system or device of any one or more of clauses 31-36, wherein each of the return electrodes is configured to be releasably securable to skin of the patient.

38. The system or device of any one or more of clauses 31-37, wherein the controller includes circuitry through which the electrical energy is distributed to the plurality of return electrodes.

39. The system or device of any one or more of clauses 31-38, wherein the controller includes a plurality of transformers, each transformer in electrical communication with a respective pair of the return electrodes.

40. The system or device of any one or more of clauses 31-39, wherein the controller includes one or more resistors and one or more switches, the one or more switches actuatable to change a path of the electrical energy between the one or more resistors and the plurality of return electrodes.

41. The system or device of any one or more of clauses 31-40, wherein the controller is configured to time-divide the electrical energy between the at least one ablation electrode and the plurality of return electrodes.

42. The system or device of clause 41, wherein the controller includes a multiplexer.

43. The system or device of clause 42, wherein the multiplexer includes a make-before-break switch.

44. The system or device of any one or more of clauses 31-42, wherein the at least one generator includes a plurality of generators electrically isolated from one another, and the controller is configured to control each generator to drive electrical energy between the at least one ablation electrode and a respective return electrode.

45. The system or device of clause 44, wherein the generators of the plurality of generators are electrically isolated from one another over a predetermined frequency range.

46. A tissue ablation system or device of any one or more of clauses 31-45 for use in a method of ablating tissue, the method comprising:
 delivering electrical energy from the least one ablation electrode to tissue at a treatment site within an anatomic structure of a patient;
 receiving the electrical energy from the at least one ablation electrode at the plurality of return electrodes, the return electrodes external to the patient and in contact with the skin of the patient; and
 with the plurality of return electrodes in a fixed position in contact with the skin of the patient, controlling a distribution of the electrical energy among the plurality of return electrodes.

47. A method of controlling a distribution of the electrical energy among a plurality of return electrodes, the method comprising:
 receiving the electrical energy at the plurality of return electrodes from at least one ablation electrode which has pre-delivered electrical energy to tissue at a treatment site within an anatomic structure of a patient, the return electrodes being external to the patient and configured to be in contact with the skin of the patient; and
 with the plurality of return electrodes in a fixed position in contact with the skin of the patient, controlling a distribution of the electrical energy among the plurality of return electrodes.

48. The method of clause 47, wherein controlling the distribution of the electrical energy includes controlling a distribution of current among the plurality of return electrodes.

49. The method of any one of clauses 47 and 48, wherein controlling the distribution of the electrical energy includes controlling a distribution of voltage among the plurality of return electrodes.

50. The method of any one of clauses 47 and 48, wherein controlling the distribution of the electrical energy includes controlling power distribution among the plurality of return electrodes.

51. The method of any one or more of clauses 47-50, wherein controlling the distribution of the electrical energy among the plurality of return electrodes includes substantially uniformly distributing at least one of current and voltage of the electrical energy among the plurality of return electrodes.

52. The method of any one or more of clauses 47-51, wherein controlling the distribution of the electrical energy among the plurality of return electrodes includes maintaining an electrode current in each respective return electrode below a predetermined threshold.

53. The method of clause 52, wherein the predetermined threshold is less than about 1 ampere.

54. The method of any one or more of clauses 47-53, wherein controlling the distribution of the electrical energy among the plurality of return electrodes includes directing the electrical energy through one or more transformers, each transformer in electrical communication with at least two of the return electrodes.

55. The method of any one or more of clauses 47-54, wherein controlling the distribution of the electrical energy among the plurality of return electrodes includes switching a path of the electrical energy through one or more resistors in electrical communication with one or more of the return electrodes.

56. The method of any one or more of clauses 47-55, wherein controlling the distribution of the electrical energy among the plurality of return electrodes includes time-division multiplexing the electrical energy between the at least one ablation electrode and the plurality of return electrodes.

57. The method of clause 56, wherein the electrical energy is time-division multiplexed between the at least one ablation electrode and each return electrode.

58. The method of any one or more of clauses 56 and 57, wherein time-division multiplexing the electrical energy between the at least one ablation electrode and the plurality of return electrodes includes make-before-break switching between the return electrodes.

59. The method of any one or more of clauses 47-58, wherein controlling the distribution of the electrical energy among the plurality of return electrodes includes generating the electrical energy from a plurality of generators, each generator electrically isolated from each of the other generators, and each generator associated with a respective one of the return electrodes and the at least one ablation electrode.

60. The method of clause 59, wherein each generator is electrically isolated from each of the other generators over only a predetermined frequency range.

61. A tissue ablation system or device of any one or more of clauses 31-45 for use in a method of controlling a distribution of the electrical energy among a plurality of return electrodes, the method comprising:
receiving the electrical energy at the plurality of return electrodes from at least one ablation electrode which has pre-delivered electrical energy to tissue at a treatment site within an anatomic structure of a patient, the return electrodes being external to the patient and configured to be in contact with the skin of the patient; and
with the plurality of return electrodes in a fixed position in contact with the skin of the patient, controlling a distribution of the electrical energy among the plurality of return electrodes.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Absent an explicit indication to the contrary, the disclosed steps may be modified, supplemented, omitted, and/or re-ordered without departing from the scope of this disclosure. Further, the various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A tissue ablation system, comprising:
a catheter comprising an ablation electrode configured to positioned at a target treatment site within a patient;
a plurality of return electrodes positionable on skin of the patient;
a generator, wherein the generator is in electrical communication with and configured to drive electrical energy between the ablation electrode and the plurality of return electrodes; and
a processing circuitry including one or more transformers in electrical communication with the ablation electrode, the plurality of return electrodes, and the generator, wherein each transformer of the processing circuitry is in electrical communication with a pair of the plurality of return electrodes,
wherein the processing circuitry is configured to substantially uniformly distribute at least one of the current and the voltage of the electrical energy through the one or more transformers with the plurality of return electrodes in a fixed position on the skin of the patient and without manual intervention of the plurality of return electrodes.

2. The system of claim 1 wherein the processing circuitry is configured to control distribution of current of the electrical energy among the plurality of return electrodes.

3. The system of claim 1 wherein the processing circuitry is configured to control distribution of voltage of the electrical energy among the plurality of return electrodes.

4. The system of claim 1 wherein the processing circuitry is configured to maintain at least one of an electrode current and an electrode voltage in each return electrode of the plurality of return electrodes below a predetermined threshold.

5. The system of claim 4 wherein the predetermined threshold is less than about 1 ampere.

6. A system, comprising:
a catheter comprising an ablation electrode configured to be intravascularly delivered within an anatomic structure of a patient;
a plurality of return electrodes positionable on skin of the patient;
a generator external to the patient and in electrical communication with the ablation electrode and the plurality of return electrodes, wherein the generator is configured to drive electrical energy between the ablation electrode and the plurality of return electrodes; and
a network of one or more transformers in electrical communication with the ablation electrode, the plurality of return electrodes, a processor, and the generator, wherein each transformer of the network is in electrical communication with a pair of the plurality of return electrodes,
wherein the processor determines a substantially uniform distribution, and
wherein the network is configured to substantially uniformly distribute at least one of the current and the voltage of the electrical energy through the one or more transformers in electrical communication with the plurality of return electrodes (i) with the plurality of return electrodes in a fixed position on the skin of the patient and (ii) without manual intervention with the plurality of return electrodes based on the substantially uniform distribution.

7. The system of claim 6 wherein the network is configured to control distribution of current of the electrical energy among the plurality of return electrodes based on the substantially uniform distribution.

8. The system of claim 6 wherein the network is configured to control distribution of voltage of the electrical energy among the plurality of return electrodes based on the substantially uniform distribution.

9. The system of claim 6 wherein the processor is configured to control the network to maintain at least one of an electrode current and an electrode voltage in each return electrode of the plurality of return electrodes below a predetermined threshold.

10. The system of claim 9 wherein the predetermined threshold is less than about 1 ampere.

11. The system of claim 6 wherein each of the plurality of return electrodes is releasably securable to skin of the patient.

12. The system of claim 6 wherein the network comprises circuitry through which the electrical energy is distributed to the plurality of return electrodes.

13. The system of claim 6 wherein:
the network comprises one or more resistors and one or more switches, and
the one or more switches are actuatable to change a path of the electrical energy between the one or more resistors and the plurality of return electrodes.

14. The system of claim 6 wherein the network is configured to time-divide the electrical energy between the ablation electrode and the plurality of return electrodes.

15. The system of claim 6 wherein the network further comprises a multiplexer.

16. The system of claim 15 wherein the multiplexer includes a make-before-break switch.

17. The system of claim 6, further comprising an additional generator electrically isolated from the generator, and wherein the network is configured to control the generator and the additional generator to drive electrical energy between the ablation electrode and a respective return electrode.

18. The system of claim 17 wherein the generator and the additional generator are electrically isolated from each other over a predetermined frequency range.

19. A method of ablating tissue of a patient, the method comprising:
delivering electrical energy to target tissue at a treatment site within the patient via an ablation electrode;
receiving the electrical energy from the ablation electrode at a plurality of return electrodes positioned in contact with an external skin surface of the patient; and
controlling a distribution of the electrical energy among the plurality of return electrodes to substantially uniformly distribute at least one of the current and the voltage of the electrical energy among the plurality of return electrodes,
wherein controlling the distribution of the electrical energy among the plurality of return electrodes includes directing the electrical energy through one or more transformers, each transformer in electrical communication with at least two of the plurality of return electrodes.

20. The method of claim 19 wherein delivering electrical energy to target tissue at a treatment site within the patient comprises ablating tissue in a cardiac chamber of the patient.

21. The method of claim 19 wherein controlling the distribution of the electrical energy includes controlling power distribution among the plurality of return electrodes.

22. The method of claim 19 wherein controlling the distribution of the electrical energy includes controlling a distribution of current among the plurality of return electrodes.

23. The method of claim 19 wherein controlling the distribution of the electrical energy includes controlling a distribution of voltage among the plurality of return electrodes.

* * * * *